US012167830B2

(12) United States Patent
Ulmschneider et al.

(10) Patent No.: US 12,167,830 B2
(45) Date of Patent: *Dec. 17, 2024

(54) VIDEO ENDOSCOPE WITH A ROTATABLE COUPLING POINT

(71) Applicant: KARL STORZ SE & Co KG, Tuttlingen (DE)

(72) Inventors: Daniel Ulmschneider, Tuttlingen (DE); Andreas Heni, Tuttlingen (DE); Markus Kupferschmid, Tuttlingen (DE); Lawrence Natusch, Tuttlingen (DE)

(73) Assignee: KARL STORZ SE & Co KG, Tuttlingen (DE)

( * ) Notice: Subject to any disclaimer, the term of this patent is extended or adjusted under 35 U.S.C. 154(b) by 78 days.

This patent is subject to a terminal disclaimer.

(21) Appl. No.: 18/077,195

(22) Filed: Dec. 7, 2022

(65) Prior Publication Data

US 2023/0108695 A1    Apr. 6, 2023

Related U.S. Application Data

(63) Continuation of application No. 16/906,264, filed on Jun. 19, 2020, now Pat. No. 11,547,280.

(30) Foreign Application Priority Data

Jun. 22, 2019    (DE) .......................... 102019004433.9

(51) Int. Cl.
*A61B 1/00*    (2006.01)
*A61B 1/05*    (2006.01)
(Continued)

(52) U.S. Cl.
CPC ...... *A61B 1/00066* (2013.01); *A61B 1/00009* (2013.01); *A61B 1/00018* (2013.01);
(Continued)

(58) Field of Classification Search
CPC ............ A61B 1/00066; A61B 1/00009; A61B 1/00018; A61B 1/00027; A61B 1/00124;
(Continued)

(56) References Cited

U.S. PATENT DOCUMENTS 4,404,964 A * 9/1983 Kambara ........... A61B 1/00124
396/17
4,414,608 A * 11/1983 Furihata ............. A61B 1/00124
396/17
(Continued)

FOREIGN PATENT DOCUMENTS

EP          3753473 A1 * 12/2020   ......... A61B 1/00009
WO    WO-2021242736 A1 * 12/2021   ......... A61B 1/00082

*Primary Examiner* — Anh Tuan T Nguyen
*Assistant Examiner* — Shankar Raj Ghimire
(74) *Attorney, Agent, or Firm* — David N. Villalpando; Jacqueline Cohen (57) ABSTRACT

A video endoscope that includes a handle with a housing and an interface portion rotatably mounted relative to the housing, and an elongate shaft with one or more electronic image sensors, wherein a proximal end section of the shaft is detachably connected to the interface portion of the handle, where the interface portion includes a first connector element electrically connected to an electric transmission element of the interface portion and the shaft includes a second connector element electrically connected to the one or more electronic image sensors, the first and second connector elements co-operating to form a detachable electrical connection, and where the handle includes an electrical connection assembly arranged at an exterior of the interface portion forming an electrical connection to at least one stationary electric and/or electronic component of the handle in a multiplicity of rotational positions of the interface portion relative to the housing.

20 Claims, 6 Drawing Sheets

(A-A)

(51) Int. Cl.
*A61B 1/06* (2006.01)
*A61B 90/00* (2016.01)
*G02B 23/24* (2006.01)
*H01R 39/64* (2006.01)
*H04N 23/54* (2023.01)
*H04N 23/50* (2023.01)

(52) U.S. Cl.
CPC ...... *A61B 1/00027* (2013.01); *A61B 1/00124* (2013.01); *A61B 1/05* (2013.01); *A61B 1/053* (2013.01); *A61B 1/0661* (2013.01); *A61B 1/0669* (2013.01); *A61B 1/0684* (2013.01); *A61B 90/03* (2016.02); *G02B 23/2484* (2013.01); *H01R 39/643* (2013.01); *H04N 23/54* (2023.01); *A61B 2090/035* (2016.02); *H01R 2201/12* (2013.01); *H04N 23/555* (2023.01)

(58) Field of Classification Search
CPC ......... A61B 1/05; A61B 1/053; A61B 1/0661; A61B 1/0669; A61B 1/0684; A61B 90/03; A61B 2090/035; A61B 1/00042; A61B 1/00105; A61B 1/00073; G02B 23/2484; H01R 39/643; H01R 2201/12; H04N 23/54; H04N 23/555
See application file for complete search history.

(56) References Cited

U.S. PATENT DOCUMENTS

| | | | | |
|---|---|---|---|---|
| 5,311,859 | A * | 5/1994 | Monroe | A61B 1/042 396/17 |
| 8,723,936 | B2 * | 5/2014 | Amling | A61B 1/0676 348/65 |
| 9,907,457 | B2 * | 3/2018 | Grant | A61B 1/051 |
| 10,051,166 | B2 * | 8/2018 | Duckett, III | A61B 1/00105 |
| 10,582,833 | B2 * | 3/2020 | Mihalca | A61B 1/00029 |
| 11,185,216 | B2 * | 11/2021 | Heni | A61B 1/053 |
| 2003/0050534 | A1 * | 3/2003 | Kazakevich | A61B 1/0607 600/179 |
| 2006/0171693 | A1 * | 8/2006 | Todd | G03B 29/00 396/17 |
| 2006/0287576 | A1 * | 12/2006 | Tsuji | A61B 1/00105 600/132 |
| 2008/0009675 | A1 * | 1/2008 | Kura | A61B 1/005 600/128 |
| 2010/0188493 | A1 * | 7/2010 | Kanzaki | A61B 1/0676 348/75 |
| 2011/0018988 | A1 * | 1/2011 | Kazakevich | G02B 23/2484 348/E7.085 |
| 2011/0193948 | A1 * | 8/2011 | Amling | A61B 1/00029 348/E7.085 |
| 2014/0107416 | A1 * | 4/2014 | Birnkrant | A61B 1/00124 600/110 |
| 2014/0221749 | A1 * | 8/2014 | Grant | A61B 1/015 600/109 |
| 2014/0275780 | A1 * | 9/2014 | Feingold | A61B 1/042 600/117 |
| 2014/0309491 | A1 * | 10/2014 | Karasawa | A61B 1/00016 600/103 |
| 2016/0128550 | A1 * | 5/2016 | Laser | A61B 1/042 600/109 |
| 2016/0359286 | A1 * | 12/2016 | Gerber | H01R 39/643 |
| 2017/0318205 | A1 * | 11/2017 | Duckett, III | A61B 1/07 |
| 2017/0354316 | A1 * | 12/2017 | Mihalca | A61B 1/00126 |
| 2019/0246884 | A1 * | 8/2019 | Lu | A61B 1/018 |
| 2020/0046213 | A1 * | 2/2020 | Bendory | A61B 1/233 |
| 2021/0330176 | A1 * | 10/2021 | Thuemen | H05K 1/147 |
| 2021/0338052 | A1 * | 11/2021 | Ouyang | A61B 1/00128 |
| 2021/0378488 | A1 * | 12/2021 | Hijikata | A61B 1/00013 |

* cited by examiner

VIDEO ENDOSCOPE WITH A ROTATABLE COUPLING POINT

CROSS REFERENCE TO RELATED APPLICATIONS

This application is a continuation of U.S. patent application Ser. No. 16/906,264, filed Jun. 19, 2020, and entitled "Rotatable and Detachable Electrical Coupling Point," now issued as U.S. U.S. Pat. No. 11,547,280 on Jan. 10, 2023, which in turn claims priority to German Patent Application No. 102019004433.9, filed Jun. 22, 2019, and entitled, "Video endoscope and handle for a video endoscope," both of which are incorporated herein by reference. This application is further related in subject matter to U.S. patent application Ser. No. 16/906,947, filed Jun. 19, 2020, and issued as U.S. Pat. No. 11,185,216, issued Nov. 30, 2021, and entitled "Video Endoscope and Handle for a Video Endoscope Including Rotational Support Means," which is incorporated herein by reference. Further, this application is related in subject matter to U.S. patent application Ser. No. 16/906,978, filed Jun. 19, 2020, and entitled "Video Endoscope and Handle, Including Driven Rotation Limitation, for Video Endoscope," now issued as U.S. Pat. No. 11,672,405 on Jun. 13, 2023, which is also incorporated herein by reference.

FIELD OF THE INVENTION

The present invention relates to a video endoscope, preferably to a video endoscope used for medical procedures. The present invention also relates to a handle for a video endoscope as well as the coupling point between the video endoscope and the handle.

BACKGROUND OF THE INVENTION

Endoscopes typically comprise an elongate shaft and a handle, the shaft being configured for being inserted into an internal cavity of a human or animal body or another object to be viewed endoscopically. The elongate shaft may be rigid or flexible. The handle is designed for being held by a user during an endoscopic procedure and may have control elements for controlling various functions of the endoscope, the handle remaining outside the cavity. The endoscope comprises an optical system for generating an image of an object field in the cavity of the body or object. In video endoscopes the generated image is picked up by an electronic image sensor and displayed on a monitor. According to a widespread type of video endoscopes, the electronic image sensor is arranged in a distal (i.e. distant from the user) end section of the shaft, and an image signal generated by the image sensor is transmitted electrically towards a proximal (i.e. close to the user) end section of the endoscope for the endoscopic image to be displayed on a monitor.

During endoscopic procedures it is frequently required to change a rotational orientation of the endoscope. For example, oblique-view endoscopes are known which have a viewing direction that deviates from a longitudinal axis of the shaft, and which permit observing different object fields within the body cavity by adjusting a rotational orientation of the shaft. As it may be preferable, for example for ergonomic reasons, to keep an orientation of the handle unchanged during rotation of the shaft, the endoscope may be configured such that the shaft is rotatable with respect to the handle, and while the viewing direction of the oblique view endoscope will change, the image orientation is unaffected by the rotation of the shaft in an endoscope having a traditional rod lens system, wherein the image is detected by a non-rotating image sensor located in the handle.

In a video endoscope having the electronic image sensor fixedly mounted in the shaft, the image sensor will rotate when the shaft is rotated, and thus a rotation of the shaft will cause a rotation of the image displayed on the monitor. The rotating image shown on the monitor makes navigation by the user inside the cavity more difficult, which may lead to a prolongation of the endoscopic procedure and may increase a risk involved in a medical endoscopic intervention. Therefore, it is known to provide an image processing unit configured for erecting the image displayed on the monitor to be viewed by the user.

In US 2010/0125166 A1 a sideways looking video endoscope is disclosed that has a rigid endoscope tube and an image sensor provided on a distal end of the endoscope shaft. By rotating a wheel arranged on a proximal end of the shaft, the image can be rotated.

According to EP 2 428 155 B1 relating to a wireless camera coupling with rotatable coupling, a system is provided including an endoscope and a detachable camera head. The endoscope is provided with a transponder/transceiver and the detachable camera head is provided with a corresponding transponder/transceiver such that electrical power is transmitted from the camera head to the endoscope. Further, image data generated by the endoscope via a CCD or CMOS device may also be wirelessly transmitted from the endoscope to the detachable camera head.

As disclosed in U.S. Pat. No. 8,187,171 B2, a video endoscope comprises an elongate shaft having a longitudinal axis, and a handpiece at the proximal end of the shaft, a distal end of the shaft being provided with an electronic image sensor. The image sensor is connected, via an electrical connection extending along the shaft, to an electrical connector piece arranged on the handpiece. The image sensor and the connector piece can rotate relative to each other about the longitudinal axis of the shaft. The electrical connection comprises at least one flexible, elongate circuit board, which is able to twist about its longitudinal direction and has at least one conductor track.

In U.S. Pat. No. 9,907,457 B2 an endoscope is described that has a pannable camera at the distal end of its insertion shaft, the pannable camera assembly being pivotable to provide a range of a field of view that can be equal to or greater than 180 degrees. A distal section of the endoscope handle may be rotatable relative to a proximal hand-held section of the endoscope handle, a rotary encoder being provided to convert the rotational position of the insertion shaft relative to the handle into a signal for the purpose of image orientation correction by an electronic processor.

In known video endoscopes of the type mentioned above, transmission of electric energy and/or signals between the electronic image sensor and the handle has proven disadvantageous, in particular in terms of efficiency and reliability. Further, handling of the video endoscope before, during and/or after an endoscopic intervention, as well as image erection in order to ease navigation have shown to be not always optimal. Moreover, such endoscopes usually are not suitable for being subjected to high-pressure steam and thus, in particular, are not autoclavable.

It is therefore an object of the present invention to provide a video endoscope which alleviates at least one of the above-mentioned problems. In particular, it is an object of the invention to provide a video endoscope that permits improved handling and orientation for a user, frequently in a manner to which the user has become accustomed, while at the same time ensuring a high level of operational safety and durability. It is also an object of the present invention to provide a handle for a video endoscope.

BRIEF DESCRIPTION OF THE INVENTION

A video endoscope according to the present invention is preferably designed for medical applications, such as, for example, minimally invasive surgery and/or medical examinations. A user of the video endoscope therefore typically is a surgeon conducting an endoscopic intervention. However, the present invention may also be applicable in video endoscopes designed for non-medical purposes, for example in industrial endoscopes or borescopes.

A video endoscope according to the present invention comprises a handle, the handle comprising a housing and an interface portion rotatably mounted relative to the housing. The housing may have a size and shape suitable for being held by a user with one hand during an endoscopic intervention; the handle may as well comprise, for example, a grip to be held by the user, the grip being connected to the housing. Preferably the handle also exhibits one or more control elements for controlling various functions of the endoscope, the control elements being arranged to be operated by the user with one or more fingers of the same hand holding the handle. The handle comprises at least one stationary electric and/or electronic component, which may be fixedly mounted to and contained in the housing and is not or substantially not participating in a rotation of the interface portion relative to the housing. In the following the at least one stationary electric and/or electronic component is briefly denoted "stationary electronics", although it is to be understood that it may consist solely of cables and/or electric leads and/or a printed circuit board having conductor tracks to provide an electrical connection to an external supply and control system. Preferably, however, the stationary electronics comprises processing means, for example image pre-processing circuitry, and/or a supply unit for supplying electric energy to the image sensor mentioned below. The stationary electronics may as well comprise the control elements and corresponding circuitry. The handle may have a port for electrically connecting to the external supply and control system and/or to a monitor. The external supply and control system may comprise an image processing unit, a monitor for displaying the endoscopic image provided by the image sensor, and/or a power supply, for example.

The interface portion is rotatably mounted relative to the housing, having a rotation axis defined by its rotation with respect to the housing. The interface portion has an exterior, which may be an outer surface of a body of the interface portion. In particular, the exterior of the interface portion may be formed by such an outer surface of the interface portion that is approximately rotationally symmetric with respect to the rotation axis. The exterior may be or comprise a continuous surface or may be discontinuous. The interface portion may comprise an interior hollow space. The interface portion may be mounted at or in the housing; in particular it may be mounted in an opening or a partially open cavity of the housing such that a section of its exterior forms a part of an exterior of the handle. However, at least a section of the exterior of the interface portion may be enclosed or encompassed by the housing of the handle.

The video endoscope according to the present invention further comprises an elongate shaft configured for being inserted into a cavity to be viewed endoscopically, in particular to be inserted into a body cavity of a human or animal body. The shaft may be formed by a rigid tube, and thus the video endoscope may be a rigid video endoscope; however, the present invention may as well relate to video endoscopes having a flexible shaft. The shaft may comprise channels for irrigation and/or working instruments, for example. The shaft comprises an electronic image sensor arranged for picking up an image of an object field, the image being generated by an objective lens system. The objective lens system may be arranged at or in a distal end section of the shaft such that the image is generated on an image sensing surface of the image sensor. The objective lens system may comprise one or more lenses and other optical elements, such as an aperture stop or plate elements such as filters, polarizers, retarders or wave plates. The electronic image sensor may be, for example, a charge-coupled device (CCD) or a complementary metal-oxide semiconductor (CMOS). The image sensor is configured to convert the captured image into an electrical image signal.

In some preferred embodiments the electronic image sensor is arranged in the distal end section of the shaft, and electric lines such as a cable or a flexible printed circuit board may be provided extending through the shaft in order to supply electric energy and/or control signals to the electronic image sensor and for transferring the image signal to a proximal end section of the shaft. In alternative embodiments of the invention, the image sensor may be positioned in the proximal end section of the shaft, and image light collected by the objective lens system may be passed from the distal end section of the shaft to the proximal end section, where the image sensor captures the image transferred thereto. In these embodiments an optical image transmission system comprising, for example, rod lenses is generally used to transfer the image light from the distal end section of the shaft to the proximally located image sensor. These embodiments are particularly advantageous when the diameter of the endoscopic shaft must be narrower than is possible with a distally placed image sensor.

The video endoscope according to the present invention may also comprise more than one image sensor, either distally or proximally located. Dual image sensors are particularly advantageous for performing stereo endoscopy to permit the generation of 3D images. It is to be understood that the present disclosure relates not only to a single, but as well to a multiplicity of image sensors, for example two, three or even more image sensors.

In accordance with the present invention, the proximal end section of the shaft is detachably connected to the interface portion of the handle. In particular, the shaft is connected at its proximal end to the interface portion. Preferably the shaft is non-rotatably connected to the interface portion. The shaft is therefore rotatable in conjunction with the interface portion with respect to the housing and is thus rotatable about the rotation axis of the interface portion relative to the housing. The shaft may be configured and connected to the interface portion such that a longitudinal axis of the shaft is substantially aligned with the rotation axis of the interface portion and the shaft therefore is rotatable about its longitudinal axis, together with the interface portion, relative to the housing; alternatively, the shaft may be configured and connected such that a longitudinal axis of the shaft forms an angle to the rotation axis of the interface portion. By being detachably connected, the shaft can be easily separated from the interface portion and, in particular, can be detached without requiring a tool, and most preferably can be detached by the user during or immediately before or after an endoscopic intervention.

Further in accordance with the present invention, the interface portion comprises a first connector element that is electrically connected to an electric transmission element of the interface portion, and the shaft comprises a second connector element that is electrically connected to the electronic image sensor, the first and second connector elements co-operating and being connected to form a detachable electrical connection between the electric transmission element of the interface portion and the electronic image sensor. In particular, the first and second connector elements are configured for transmitting the electrical image signal generated by the electronic image sensor to the electric transmission element of the interface portion and for transmitting electric energy and/or control signals from the electric transmission element of the interface portion to the electronic image sensor arranged in the shaft. In this sense the first and second connector elements are configured for electrically connecting the interface portion to the electronic image sensor via a detachable electrical interface. The electric transmission element of the interface portion may be, for example, a printed circuit board having conductor tracks to transmit electric signals and/or energy. The interface portion is configured, in particular, to comprise no control elements operable by a user, and/or no electronic elements; alternatively, the electric transmission element of the interface portion may comprise image pre-processing circuitry, for example.

Furthermore, in accordance with the present invention, the handle comprises an electrical connection assembly arranged at the exterior of the interface portion, forming an electrical connection in a multiplicity of rotational positions of the interface portion relative to the housing. The electrical connection assembly forms an electrical connection between the electric transmission element of the rotatable interface portion and the stationary electronics of the handle, which is substantially non-rotating when the interface portion is rotated. The electrical connection assembly may have a first end that is connected to or is configured to contact the exterior, for example connected to or contacting an outer surface of the interface portion, and a second end that is connected to the stationary electronics of the handle, the first and second ends electrically connected to each other. The electrical connection assembly is configured to maintain the electrical connection in various rotational positions of the interface portion relative to the housing. In particular, the electrical connection assembly may be configured to provide the electrical connection independent of the rotational position or of a corresponding rotation angle of the interface portion, at least in a given range of rotational positions. The electrical connection assembly is configured for transmission of the electrical image signal from the electric transmission element of the interface portion to the stationary electronics of the handle, and/or for transmitting electric energy from the stationary electronics of the handle to the electric transmission element of the interface portion.

Due to the interface portion being rotatable relative to the housing of the handle, it is thus possible for a user to rotate the shaft relative to the housing of the handle and thereby, for example, to adjust a viewing direction of the endoscope while holding the handle in a fixed orientation. Further, configuring the endoscope is facilitated by the shaft being detachably connected to the handle. Moreover, due to the arrangement of the electrical connection assembly, forming an electrical connection in a multiplicity of rotational positions of the interface portion, an electrical connection between the stationary electric and/or electronic element in the handle and the electronic image sensor can be established and maintained in a multiplicity of rotational positions of the shaft or, in particular, in any orientation of the shaft relative to the housing of the handle, at least within a given range of rotational positions. The user is therefore free to choose a suitable orientation of the shaft without substantially impeding the electrical connection between the image sensor and an image processing unit arranged in the handle or in an external system, and thus providing uninterrupted endoscopic view. The arrangement of the electrical connection assembly at the exterior of the rotatable interface portion permits a space-saving arrangement and thus a compact and ergonomic design of the handle and further permits achieving a reliable and durable electric connection. Accordingly, the endoscope permits easier handling and configuration, as well as improved functionality and operational safety.

In particular, the interface portion may be configured to be permanently connected to or comprised by the housing, or to be not detachable from the housing without the need of a tool. In this sense the interface portion according to such an embodiment is not detachable from the housing, although it is rotatable, while the shaft is detachable from the interface portion, although in a connected state it is preferably not rotatable with respect to the interface portion. In this case, the functions of detachability and rotatability are separated and are provided by different components of the video endoscope, thus achieving a particularly simple and reliable design.

According to a preferred embodiment, the electrical connection assembly comprises at least one sliding contact. The sliding contact may be, for example, designed as a slip ring consisting of a brush mounted stationary with respect to the housing and contacting in a sliding manner a metal ring forming a section of the exterior or of an outer surface of the interface portion. Conversely, the sliding contact may be formed by a rotating brush contacting a stationary metal ring. Preferably the electrical connection assembly comprises two or more sliding contacts or contact elements electrically insulated from each other to provide at least as many electrical connections as are required to transmit signals and/or electric energy from and/or to the image sensor. By providing at least one sliding contact, the electrical connection can be established and maintained in any rotational position at least within a given range. Most preferably the metal ring extends over approximately 360°; in this case, the electrical connection is independent of the rotational position, wherein even an unlimited number of turns of the interface portion relative to the housing may be permissible.

According to a particularly preferred embodiment, the electrical connection assembly is arranged at or on a periphery of the interface portion. For clarity, the periphery is also denoted outer periphery in the present disclosure. According to this embodiment, therefore, the exterior of the interface portion at which the electrical connection assembly is arranged, forming an electrical connection in a multiplicity of rotational positions of the interface portion relative to the housing, is an outer periphery of the interface portion. The outer periphery may be, for example, a continuous or a discontinuous surface of a body of the interface portion. The outer periphery, or that section of the outer periphery at which the electrical connection assembly is arranged, may be formed by an outer peripheral surface of the interface portion, the outer peripheral surface being located at a radial distance from the rotation axis. The outer peripheral surface may be, at least in a section in which the electrical connection assembly is arranged, partially rotation-symmetric with respect to the rotation axis. For example, the interface portion may have an approximately cylindrical shape, wherein the axis of the cylinder approximately coincides with the rotation axis, and the outer periphery is formed by lateral surface portions of the approximately cylindrical interface portion. This embodiment permits a particularly simple design and enhances the operational reliability of the video endoscope.

According to a further preferred embodiment, the electrical connection assembly comprises at least one flexible conductor element that is configured to be spooled on and/or unspooled from the periphery of the interface portion, which may be an outer peripheral surface of the interface portion, by rotating the interface portion relative to the housing. In accordance with this embodiment, therefore, the handle comprises a flexible conductor element forming the electrical connection between the electric transmission element of the interface portion and the stationary electronics of the handle, wherein the flexible conductor element is spooled on and/or unspooled from the periphery of the interface portion by the rotation of the interface portion. In particular, the flexible conductor element is wrapped or wound around a section of the periphery or the outer peripheral surface of the interface portion when the interface portion is rotated in one direction, and wound off when the interface portion is rotated in the opposite direction. The interface portion and the flexible conductor element can therefore be considered to form a spool. The flexible conductor element may have a first end that is fixed to the outer peripheral surface and electrically connected to the electric transmission element of the interface portion, and a second end that is mounted to the housing and connected to the stationary electric and/or electronic element of the handle. Most preferably, the flexible conductor element is mounted such that twisting is avoided when it is spooled or unspooled. By providing a flexible conductor element that is spooled around the interface portion, rotation of the interface portion can be achieved with low friction, and at the same time the electric connection can be maintained in an uninterrupted manner during rotation and for any rotational position of the interface portion within a pre-defined range of rotational positions. Preferably, the interface portion and the flexible conductor element are configured such that the flexible conductor element may be wound at least 90°, at least 180°, at least 270° or at least 360° around the outer periphery of the interface portion, permitting a rotation at least in a corresponding range of rotational positions. That is, the flexible conductor element may form less than one complete winding when it is wound around the circumference of the interface portion or may form one complete winding or more than one winding; in the latter case the windings may be wound one upon the other, forming a spiral-shaped arrangement. In this way a high degree of rotational freedom and a substantially wear-free operation can be achieved, thereby enhancing the functionality and durability of the video endoscope.

According to a preferred embodiment of the present invention, the flexible conductor element is or comprises a flexible cable, a flexible ribbon cable or a flexible circuit board, or a plurality or a combination of such elements. Employing a flexible cable, flexible ribbon cable or flexible circuit board facilitates assembly of the handle and provides a reliable connection during use. Further, a ribbon cable or a flexible circuit board may comprise a multiplicity of electric leads, permitting transmission of a high data volume and/or a multiplicity of signals in parallel, as well as supplying electric energy to the image sensor. Moreover, a ribbon cable or a flexible circuit board is easy to spool, allowing a particularly simple design and reliable and reproducible operation of the endoscope.

Preferably, the housing comprises a storage or reservoir for receiving at least an unspooled portion of the flexible conductor element. In particular, the flexible conductor element may be completely contained within the housing, comprising a portion spooled on the outer periphery of the interface portion and an unspooled portion. The housing typically has a size that provides sufficient space for accommodating the reservoir. In this way entangling or blocking of the flexible conductor element during rotation can be largely avoided, thereby increasing operational reliability and safety.

According to a particularly preferred embodiment, an unspooled portion of the flexible conductor element is guided by at least one roll arranged in the reservoir, the roll having a rotational axis that preferably is substantially parallel to the rotation axis of the interface portion. In particular, the unspooled portion may be routed around the roll. The roll may be arranged to receive an unspooled portion of the flexible conductor element when the interface portion is rotated to unspool the flexible conductor element, and to make available a portion of the flexible conductor element for being spooled on the outer periphery when the interface portion is rotated in the opposite direction. According to a yet further preferred embodiment, the roll is movably arranged within the reservoir and is configured for tensioning the flexible conductor element. In particular, the roll may be spring loaded in a direction for tensioning the flexible conductor element. In this way, an unspooling movement of the flexible conductor element may be precisely controlled and entangling of the flexible conductor element can be most safely avoided. Thus, reliability and reproducibility of the operation of the endoscope can be further enhanced.

Additionally, or alternatively, at least a section of the unspooled portion of the flexible conductor element may be routed in an arc-like shape in the reservoir, and/or may be loosely arranged within the reservoir. Thus, for example, a one-sided or two-sided abutment surface may be provided for routing the flexible conductor element in the reservoir. The unspooled portion of the flexible conductor element may form consecutive or alternating arcs, such as a meandering shape. Furthermore, the flexible conductor element may be configured to be pre-bent in an elastic manner or itself be embodied as a spring. Thus the provision of a sufficient length of the flexible conductor element for being spooled can be achieved in a simple manner.

In accordance with a preferred embodiment of the present invention, the handle comprises at least two bearings for rotatably supporting the interface portion with respect to the housing, and the electrical connection assembly is arranged at an intermediate section of an outer peripheral surface of the interface portion. The intermediate section of the outer peripheral surface is a section of the outer peripheral surface that is situated between the at least two bearings. The bearings may serve to support the rotational movement of the interface portion, and moreover serve to define the arrangement of the electrical connection assembly. Thus, for example, contact between a brush and a metal ring may be enhanced, and/or spooling on the outer peripheral surface of the interface portion can be improved by the bearings being arranged on both sides of the respective section of the outer peripheral surface. In this way handling of the endoscope may be further facilitated.

Furthermore, a seal may be provided to seal an opening of the housing in which the interface portion is rotatably mounted. The seal preferably is located adjacent to a bearing such that the bearings are comprised in a sealed inner space of the housing. Most preferably, the seal is arranged at an outside direction from the above mentioned first and second bearings, such that the intermediate section of the outer peripheral surface is enclosed by the seal. Such a sealing may protect the handle, particularly any electrical and electronic components and/or connections within the handle and/or the interface portion such as, in particular, the electrical connection assembly, from body liquids or sterilization fluids. The sealing may therefore improve durability and operational safety of the endoscope.

Preferably, a range of rotation of the interface portion relative to the housing is limited by a stop. The stop may be a physical stop limiting the range of rotation to an angular range of less than 360°. The stop may serve to enhance operational safety and reliability of the endoscope and in particular to avoid damage to the endoscope by over-rotation of the interface portion relative to the housing. A stop is particularly advantageous in case of the electrical connection assembly comprising at least one flexible conductor element to be spooled and/or unspooled during rotation of the interface portion, as described above.

According to a preferred embodiment, the handle comprises at least one sensor configured for detecting a rotation angle and/or a rotational position of the interface portion relative to the housing. The sensor may be or comprise, for example, a rotary encoder, a hall sensor and/or a magnetic sensor. In particular, the sensor may be an incremental rotary encoder to generate a rotation signal that is representative of the rotation angle, or an absolute rotary encoder to generate a rotation signal representative of a rotational position of the interface portion. The rotation signal can be passed on to an image processing unit for digitally erecting the image based on the detected angle of rotation.

Most preferably, the endoscope comprises or is connectable to an image processing unit that is configured for erecting the image provided by the image sensor, depending on the rotation signal, to display an image that is independent of the rotation of the shaft. The image processing unit may be comprised in the handle or, preferably, in an external control and supply system. The endoscope may further comprise a gravity sensor for detecting rotation of the handle; the image processing unit may be configured for erecting the image, independent of an orientation of the shaft, relative to a gravity vector. In this way navigation in the cavity by a user can be facilitated.

Advantageously, the second connector element comprises a plurality of conductor pins, and the first connector element comprises a plurality of sockets configured to receive the conductor pins. Electrical energy and data signals may be suitably transmitted via a connection of pins of the shaft and corresponding sockets of the handle. In this way a compact design and an easy and reliable electrical connection between the electric transmission element of the interface portion and the electronic image sensor can be achieved. Further, the pins of the second connector element may be easy to clean after use of the video endoscope. Preferably, the first connector element is rigidly mounted to a front side of the interface portion facing the shaft, and the second connector element is rigidly mounted to the proximal end section of the shaft. In a further preferred manner, the pins and the receptacles of the sockets extend in a direction parallel to the rotation axis of the interface portion; thereby forming the electrical connection is facilitated. Most preferably, the first and second connector elements may be arranged and configured such that the electrical connection is automatically formed when the shaft is mechanically connected to the handle.

In particular, the pins of the shaft are connected to the sockets of the handle by friction fit, and thus the shaft is mechanically connected to the handle when the electrical connection is formed. The shaft may thereby be easily connected to and detached from the handle. Further, the first and second connector elements and/or further elements of the shaft and the interface portion may be configured such that the shaft can be connected to the interface portion only in a defined angular position, thereby facilitating rotation sensing by the sensor for erecting the endoscopic image.

Preferably, in addition to the first and second connector elements, a mechanical coupling mechanism may be provided to couple the shaft in a safe and stable manner to the handle. The coupling mechanism may, in particular, include a coupling element of the shaft co-operating with a corresponding coupling element of the handle, thereby avoiding inadvertently detaching the shaft from the handle, but allowing rotation of the shaft with respect to the housing of the handle. The coupling element of the handle may be arranged on a front side of the housing facing the proximal end section of the shaft, for example on a circumferential portion of the housing encompassing the interface portion, such that the interface portion of the handle is substantially or completely overlapped by the shaft and the coupling mechanism in a connected state. In this way a particularly stable coupling can be achieved. The mechanical coupling mechanism may be configured to comprise, for example, a releasable snap fit, a positive fit, a bayonet and/or a claw coupling. Handling and reliability of the connection may thereby be further improved.

According to a preferred embodiment of the invention, the shaft is hermetically sealed. In particular, the second connector element may be sealed in itself and connected in a hermetically sealed manner to the shaft; the second connector element may be, for example, inserted into a proximal end section of a tube forming the shaft and sealingly embedded in a suitable resin. The electronic image sensor may also be contained in a hermetically sealed inner space of the shaft. The shaft may further comprise open passages, for example an irrigation or instrument channel. Most preferably, the shaft is configured to be autoclavable. Due to the shaft being hermetically sealed and/or autoclavable, multiple use of the shaft may be facilitated.

Alternatively, the shaft may be configured disposable, i.e., for single use. In particular, the shaft may comprise only a small number of costly optical and electronic elements and thus may be designed to be manufactured at a comparatively low cost.

Preferably, the handle is configured for multiple use. As the handle is not introduced into a body cavity during the endoscopic intervention, the handle may or may not be autoclavable.

According to a further preferred embodiment, the shaft may comprise an electric illumination source to generate light or, for example, near-infrared radiation, for illuminating a cavity to be observed. The illumination source preferably is or comprises an LED. The illumination source may be arranged at the distal end of the shaft, or, for example, near the proximal end of the shaft and optically coupled to a light guide transmitting the illumination radiation to the distal end. The illumination source is preferably supplied with electrical energy via the interface portion, i.e., via the first and second connector elements, the electric transmission element of the interface portion, and the electrical connection assembly of the handle, as described above. A power supply for the illumination source may be provided in the housing of the handle, or an external power supply may be connectable to the handle.

Alternatively, the shaft may comprise a port for connecting a light cable of an external light source and a light guide to transmit the illumination radiation generated by the external light source to the distal end of the shaft. The port may be arranged at or near the proximal end section of the shaft and is preferably separate from the second connector element.

A further aspect of the present invention relates to a handle for a video endoscope, in particular for a medical video endoscope, preferably for a video endoscope as described above. The handle comprises a housing and an interface portion rotatably mounted relative to the housing. The interface portion may be configured for being detachably connected to a proximal end section of an elongate shaft of the video endoscope, the shaft comprising at least one electronic image sensor. The interface portion comprises a first connector element electrically connected to an electric transmission element of the interface portion, wherein the first connector element is configured to be connectable to a second connector element of the shaft of the video endoscope, to form a detachable electrical connection. The handle further comprises an electrical connection assembly arranged at an exterior, in particular at an outer peripheral surface, of the interface portion forming an electrical connection to a stationary electric and/or electronic element of the handle in a multiplicity of rotational positions of the interface portion relative to the housing. In particular, at least one flexible conductor element and/or sliding contact may be arranged at or on the exterior of the interface portion for transmitting electrical signals and/or electrical energy via the electrical interface from and/or to a shaft in different rotational positions of the interface portion relative to the housing. In particular, the handle is configured as described above.

The handle permits connecting a shaft of the video endoscope, and due to the interface portion being rotatable relative to the housing, permits rotating the shaft. At the same time, the arrangement of the electrical connection assembly arranged at the exterior of the interface portion allows establishing and maintaining an electrical connection between the shaft and further electrical and/or electronic elements or units inside the handle or exterior to the handle, in a multiplicity of rotational positions of the shaft relative to the handle. That is, the electrical connection assembly allows rotating a connected shaft and the interface portion relative to the housing without substantially impeding the electrical connection from and/or to the shaft.

According to a further aspect the present invention relates to a shaft for a video endoscope, in particular for a medical video endoscope, preferably for a video endoscope as described above. The shaft is elongate and configured for being inserted into a cavity to be viewed endoscopically and comprises at least one electronic image sensor. A proximal end section of the shaft is configured to be detachably connectable to an interface portion of a handle of the video endoscope. The proximal end section of the shaft is equipped with a second connector element electrically connectable to a first connector element of the handle. In particular, the shaft is configured as described above.

The present invention also relates to a video endoscope system, in particular a medical video endoscope system. The video endoscope system comprises at least one handle, the handle being configured as described above, and at least two shafts, each of the at least two shafts being configured as described above. Preferably, the at least two shafts are designed having different optical, mechanical and/or electrical features, such as, for example, different viewing directions, different fields of view, different lengths and/or diameters, different configurations relating to irrigation or instrument channels, different types or arrangements of image sensors and/or illumination sources. Due to the detachable connection of each shaft to the handle, shafts can be easily exchanged to adapt the video endoscope to the needs of a particular endoscopic intervention.

Further, the present invention relates to a method for operating a video endoscope, according to which method a video endoscope is provided that is configured as described above, the shaft being at a first angular position with respect to the housing of the handle, and the shaft is rotated with respect to the housing of the handle into a second angular position, wherein an electric connection between the electric transmission element of the interface portion and the stationary electric and/or electronic element of the handle is provided by the electrical connection assembly in the first and second angular positions. Preferably, the electric connection is maintained by the electrical connection assembly uninterruptedly during rotation, i.e., at all intermediate angular positions of the shaft relative to the housing of the handle. In this way an electric connection between the electronic image sensor and the stationary electronics of the handle can be provided and maintained independent of the rotation of the shaft relative to the housing of the handle.

In a method step preceding the steps mentioned, a handle and a shaft may be provided, the handle and the shaft being configured as described above; the shaft is connected to the handle electrically and mechanically, as described above, to form the video endoscope to be operated. In a subsequent method step to be performed after operation of the video endoscope, the shaft may be detached from the handle, as described above. In further steps another shaft may be connected to the handle, or the shaft and the handle may be subjected to cleaning and sterilization. Both of the shaft and the handle may be reusable, the shaft preferably being autoclavable.

The features of the invention as mentioned above and as described below apply not only in the combinations mentioned but also in other combinations or alone, without leaving the scope of the present invention.

BRIEF DESCRIPTION OF THE DRAWINGS

Further aspects of the present invention will be apparent from the figures and from the description of particular embodiments that follows.

DETAILED DESCRIPTION OF THE INVENTION

Figure 1:
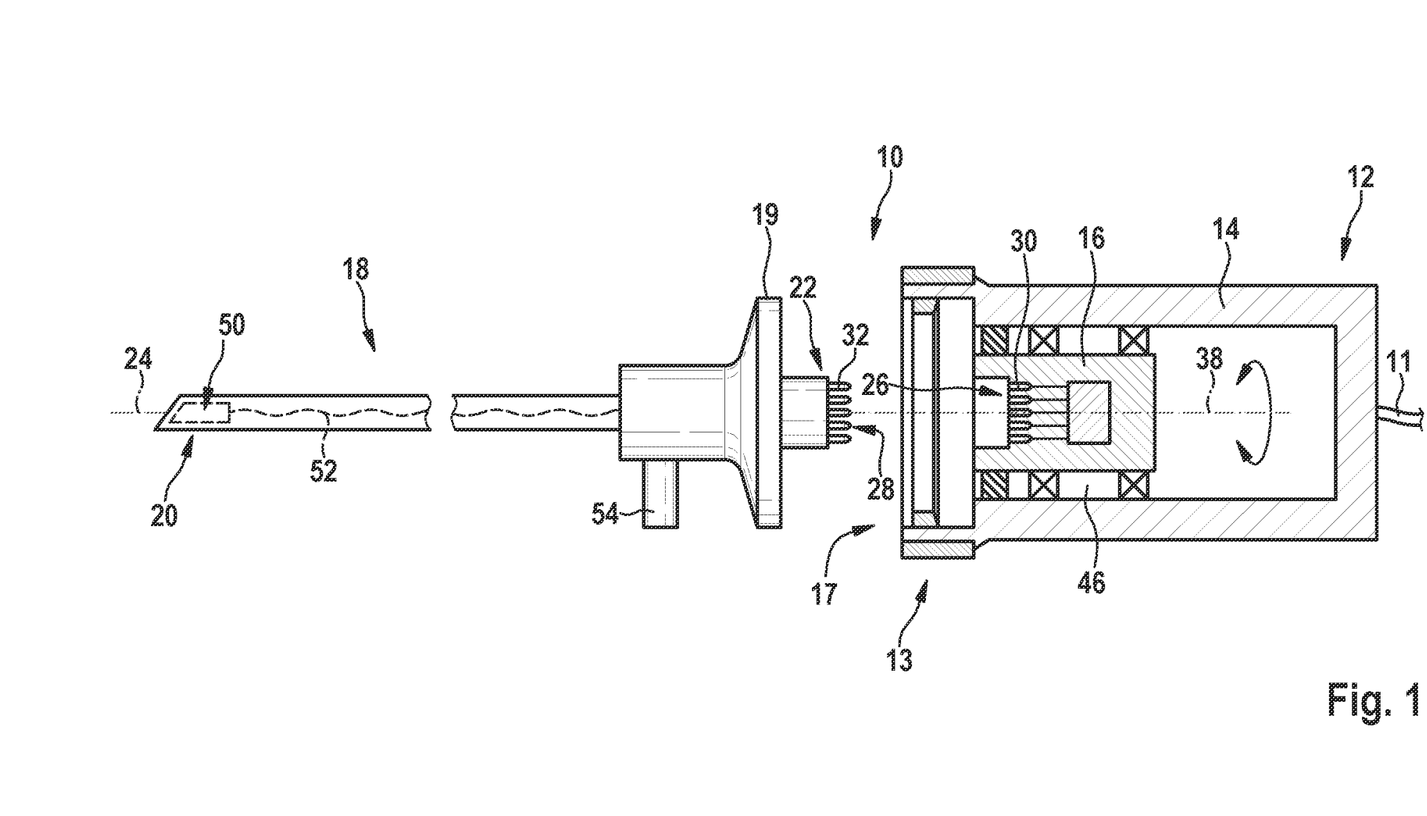
FIG. 1 shows a shaft and a handle of a video endoscope according to a first embodiment of the present invention in a detached state in a schematic, partially sectional view.
Figure 2:
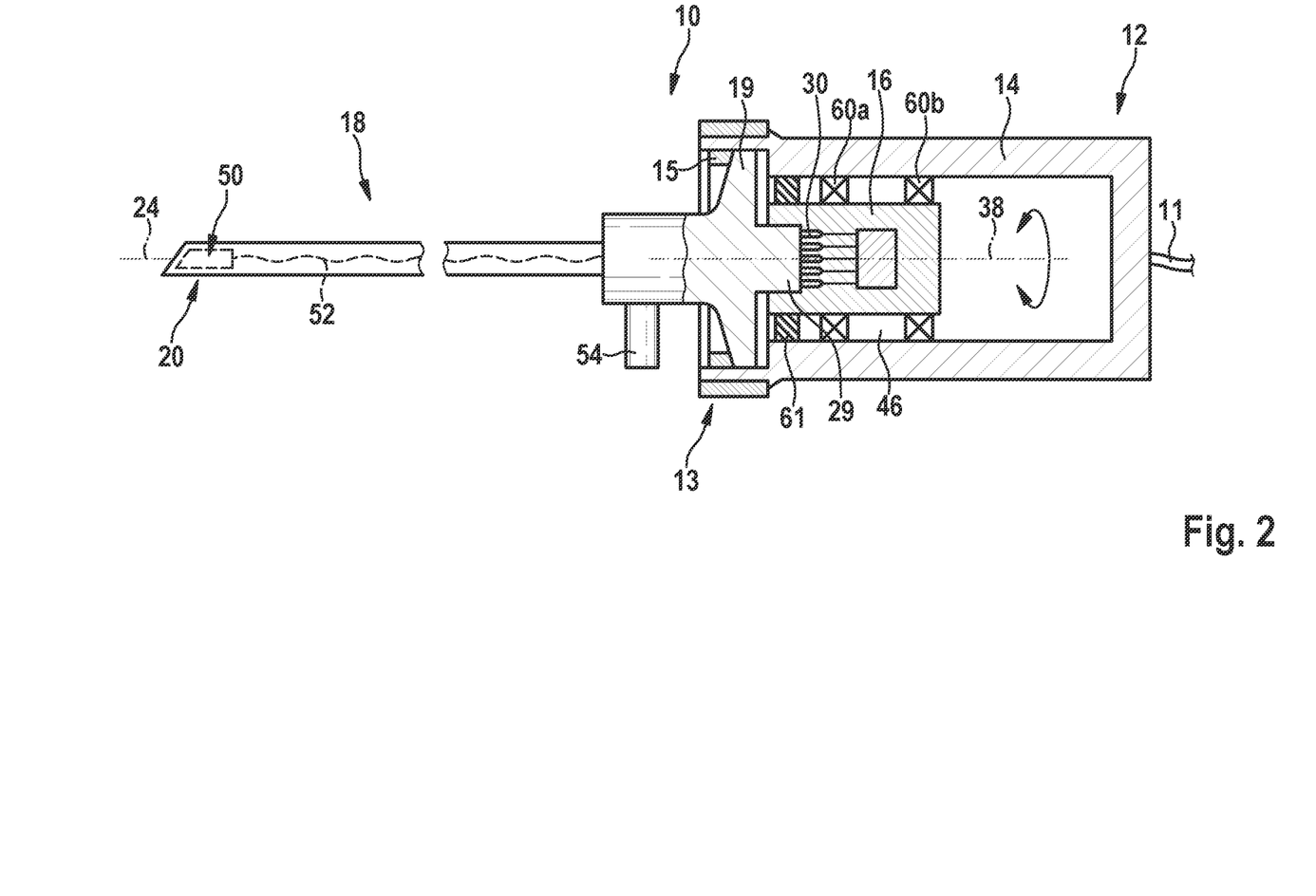
FIG. 2 shows the video endoscope according to the embodiment of FIG. 1 in a connected state.

FIGS. 1 and 2 are schematic diagrams of a video endoscope 10 according to a first embodiment of the present invention. The video endoscope 10 is designed to provide video and/or imaging data from an object field within a cavity in a human or animal body. As indicated symbolically in FIGS. 1 and 2 by cable 11, the video endoscope is connectable to an external control and supply system providing electric power and comprising image processing and display means such as a computer and a monitor. The video endoscope 10 comprises a handle 12 and a shaft 18. In FIG. 1 the handle 12 and the shaft 18 are shown in a detached state. FIG. 2 shows the video endoscope 10 of FIG. 1 in a connected state, the shaft 18 being connected to the handle 12.

The handle 12 is shown in FIGS. 1 and 2 in a schematic longitudinal sectional view. The handle 12 is sized and shaped to be held by a user of the video endoscope 10, who typically is a surgeon conducting an endoscopic intervention. The handle of the video endoscope 10 comprises a housing 14 and an interface portion 16 that is rotatably mounted relative to the housing 14. The housing 14 has a front side 17 where it has an opening in which the interface portion 16 is mounted. The housing 14 comprises a reservoir 46 for receiving a portion of a flexible circuit board 34, as is described below. For clarity, some electrical elements are omitted in FIGS. 1 and 2.

Furthermore, the video endoscope 10 comprises an elongate shaft 18 with a distal end 20, a proximal end 22, and a longitudinal axis 24 extending between the distal end 20 and the proximal end 22. The proximal end 22 of the shaft 18 is detachably connectable to the handle 12, the shaft 18 having a coupling plate 19 at its proximal end 22. As described in detail below, the shaft 18 is connected electrically and mechanically to the handle 12, the shaft 18 being rotatable with respect to the housing 14, in conjunction with the interface portion 16. In the embodiment of FIGS. 1 and 2, the longitudinal axis 24 of the shaft 18 is aligned with a rotation axis 38 of the interface portion 16. Thus, the shaft 18 is rotatable about its longitudinal axis 24 relative to the housing 14 of the handle 12.

The interface portion 16 comprises a first connector element 26, and the shaft 18 has a second connector element 28 at its proximal end 22, the first connector element 26 and the second connector element 28 co-operating to form an electrical interface for electrically connecting the handle 12 and the shaft 18. In the exemplary embodiment of FIGS. 1 and 2 the first connector element 26 comprises a plurality of sockets 30, and the second connector element 28 comprises a plurality of conductor pins 32, five sockets 30 and five pins 32 being shown symbolically in the figures. The pins 32 and the sockets 30 extend parallel to the rotation axis 38 of the interface portion, and the pins 32 can be inserted in the direction of the rotation axis 38 into the respective sockets 30.

Figure 4:
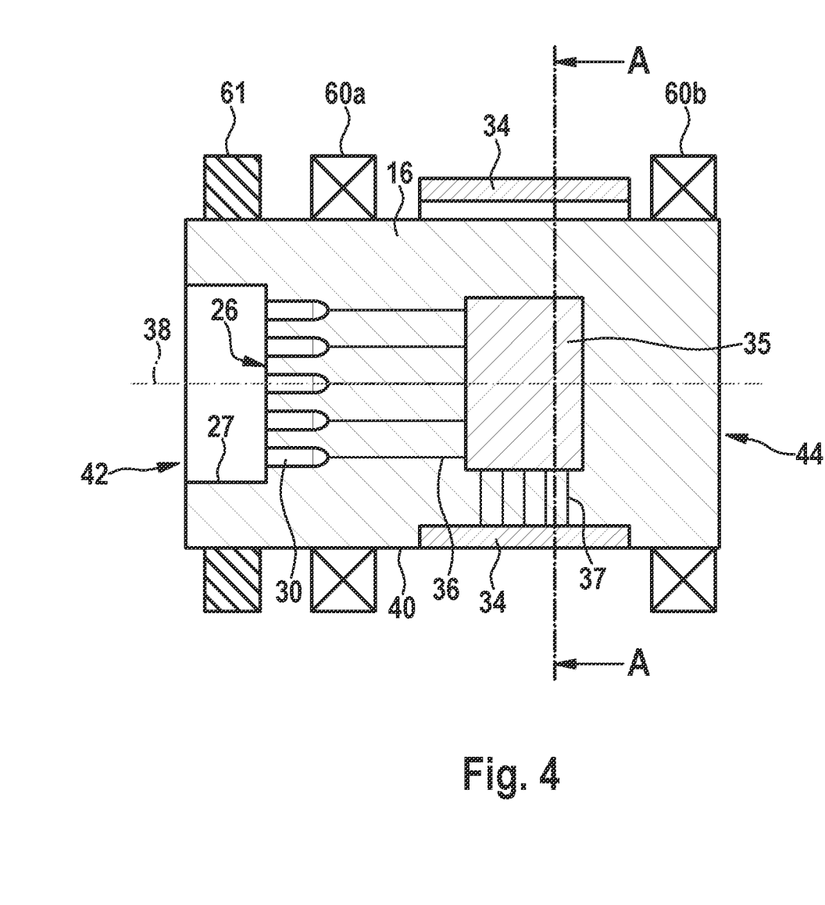
FIG. 4 is a schematic longitudinal sectional view of an interface portion of the handle of the video endoscope of FIGS. 1-3.

The first and second connector elements 26, 28 may be held to each other by friction fit of the pins 32 in the sockets 30, and/or by positive fit of the connector base 29 of the second connector element 28 in a corresponding recess 27 of the interface portion 16 (see FIG. 4). For a particularly safe and stable mechanical connection of the shaft 18 to the handle 12, in the embodiment shown a mechanical coupling mechanism 13 is provided, consisting of a claw coupling mechanism having claws 15 holding the coupling plate 19 of the shaft 18 firmly, but rotatably and releasably to the housing 14. As the first and second connector elements 26, 28 are mounted fixedly to the interface portion 16 and the shaft 18, respectively, the shaft 18 is non-rotatably connected to the interface portion 16. Embodiments employing means to fixedly connect the shaft 18 to the handle 12, such as with a claw coupling mechanism, may also employ contact means other than the pin/socket system discussed above. Such systems may employ simple contact points to make necessary electrical connections, rather than the more robust pin/socket connections.

The shaft 18 furthermore comprises an imaging unit 50 having an objective lens system and an electronic image sensor. The imaging unit 50 is arranged at or near the distal end 20 of the shaft 18. A multi-wire cable 52 extends through the shaft 18, connecting the electronic image sensor of the imaging unit 50 to the second connector element 28 at the proximal end 22 of the shaft 18. Alternatively, the electronic image sensor may be located near the proximal end 22 of the shaft 18 (see below and FIG. 3).

Furthermore, the shaft 18 comprises a stub or light post 54 forming a port for connecting a light cable of an external light source, and a light guide (not shown) extending in the shaft 18 until the distal end 20 of the shaft 18 to transmit illumination radiation provided by the external light source towards an object field to be observed. Alternatively, the shaft may comprise an LED, for example, to generate the illumination radiation, the LED being electrically connected to the second connector element 28 to be supplied with electric energy via the electric connections described.

The shaft 18 may be hermetically sealed and, in particular, may be autoclavable. To this end the second connector element 28 may be sealingly inserted into the proximal end 22 of the shaft 18. The shaft 18 may have an outer diameter of, for example, about 4 mm or about 10 mm, but may as well have any other diameter and dimension suitable for a particular medical intervention or, in case of a non-medical endoscope, an intended endoscopic investigation.

Figure 3:
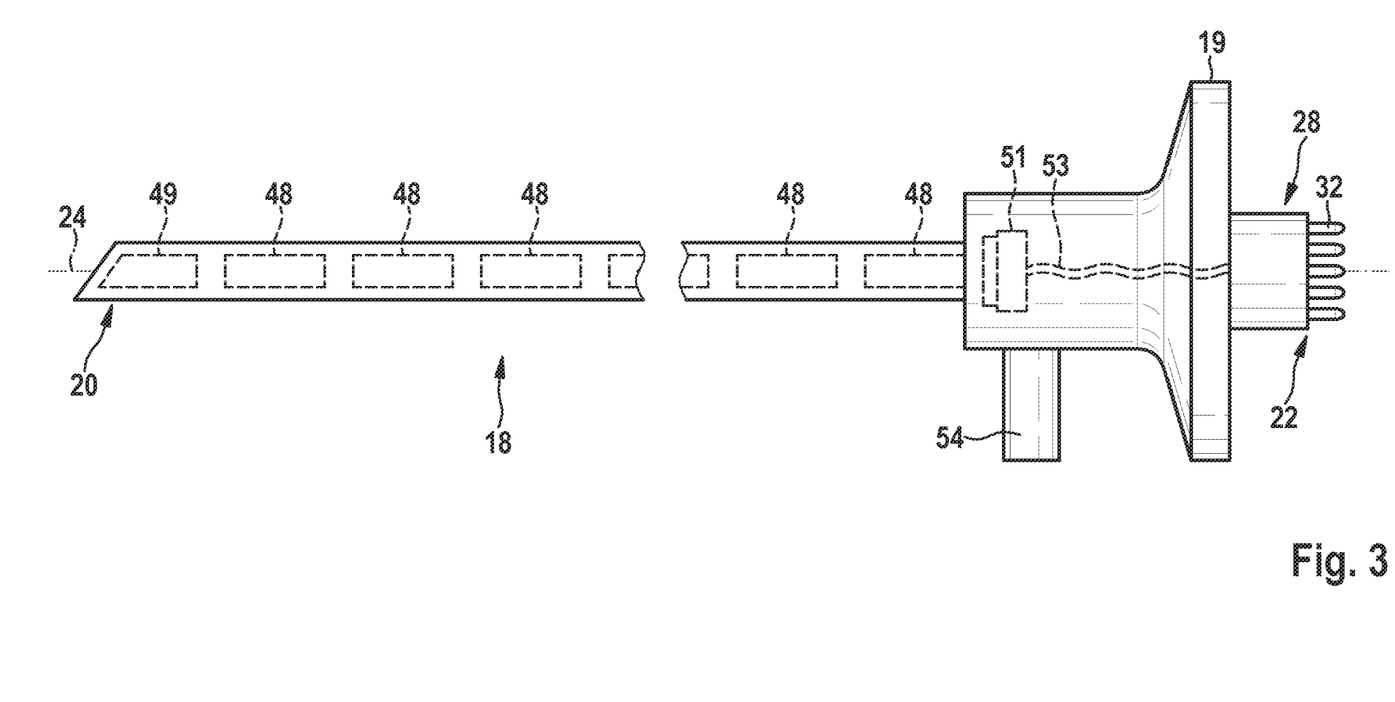
FIG. 3 shows the shaft according to a variation of the first embodiment of the present invention in a schematic, partially sectional view.

According to a variation of the first embodiment and as illustrated in FIG. 3, the shaft may comprise an electronic image sensor 51 located near the proximal end 22 of the shaft 18. The shaft 18 further comprises a rod lens system comprising a multiplicity of rod lenses 48 to transmit the image light collected by an objective lens system 49 arranged at or near the distal end 20 of the shaft 18 to the proximally arranged image sensor 51. The image sensor 51 is connected via electric leads 53 to the second connector element 28. The electric leads 53 may be formed, for example, by a multi-wire cable or by a printed circuit board. On the other hand, the image sensor 51 may form a unit with the second connector element 28, being directly connected to the second connector element 28 and not requiring electric leads 53 (not shown). As can be seen in FIG. 3, due to its location near the proximal end 22 of the shaft 18, the image sensor 51 may have a larger dimension than would be possible if it was arranged at or near the distal end 20. Further, the shaft 18 according to FIG. 3 may be configured as described above with reference to FIGS. 1 and 2 and is connectable to the handle 12 as described above.

Figure 5:
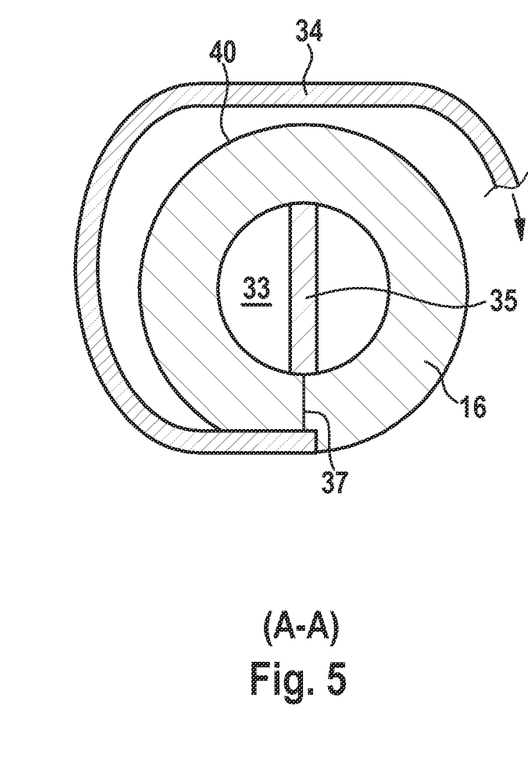
FIG. 5 is a schematic cross sectional view of the interface portion of the handle of the video endoscope in FIGS. 1-4.

In FIGS. 4 and 5 the interface portion 16 is shown in more detail. FIG. 4 is a longitudinal sectional view, and FIG. 5 is a cross sectional view (cross section A-A in FIG. 4) of the interface portion 16.

The interface portion 16 has an approximately cylindrical shape, the axis of the cylinder approximately coinciding with the rotation axis 38 of the interface portion 16. An exterior of the interface portion 16 is formed by a front end 42 and a rear end 44, corresponding to the bases of the cylinder, and a periphery or peripheral surface 40, which corresponds to the side of the cylinder. The front end 42 is on that side of the handle 12 to which the shaft 18 is connected (see FIGS. 1 and 2), and the rear end 44 is directed towards an interior of the housing 14. In the example shown the peripheral surface 40 is a largely continuous surface, but it may as well be discontinuous and comprise gaps, for example. In the following the peripheral surface 40 is also denoted outer peripheral surface 40.

The interface portion 16 is rotatably supported in the housing 14 by a first bearing 60a and a second bearing 60b. The bearings 60a and 60b may be arranged on the outer peripheral surface 40 of the interface portion 16, as symbolically depicted in FIGS. 1, 2 and 4, but may as well be designed in any other suitable manner. The first and second bearings 60a, 60b are arranged at a distance from each other, the second bearing 60b being located near the rear end 44 of the interface portion 16. Between the first bearing 60a and the front end 42, a seal 61 is arranged on the outer peripheral surface 40 to seal the inner space of the housing 14 in which the interface portion 16 is mounted. The seal 61 may be, for example, a shaft sealing of any suitable design, or may simply be formed by an O-ring.

As shown in FIG. 4, the interface portion 16 comprises a printed circuit board (PCB) 35 arranged in a hollow space 33 of the interface portion 16. The sockets 30 of the first connector element 26 are electrically connected to the PCB 35 by a multiplicity of leads 36. Further, a flexible circuit board 34 is arranged on the outer peripheral surface 40 of the interface portion 16. Instead of the flexible circuit board 34 another flexible conductor element, such as a flexible cable or a ribbon cable, or a sliding contact or a multiplicity or a combination thereof may be arranged on the outer peripheral surface 40 of the interface portion 16 (not shown). A first end of the flexible board 34 is fixed to a section of the peripheral surface 40, where conductor tracks of the flexible board 34 are connected to the PCB 35 by leads 37. Symbolically, five leads 36 and five leads 37 are depicted in FIG. 4. A second end of the flexible board, opposite to the first end and indicated in FIG. 5 by an arrow, is connected to the stationary electronics in the housing 14 (not shown). The PCB 35 serves as an electric transmission element and comprises conductor tracks to connect the leads 36 to the leads 37, thus redirecting the electrical connections, and preferably does not comprise any electronic components.

The flexible circuit board 34 is able to adapt to the shape of the peripheral surface 40 and may section-wise lie against the peripheral surface 40 or at a radial distance from the peripheral surface 40. In the situation depicted in FIG. 5, the flexible circuit board 34 is fixed to the peripheral surface 40 of the interface portion 16 at its first end, while further sections of the flexible circuit board 34 are loosely arranged within the reservoir 46 of the housing 14 (see FIG. 1). As may be comprehended from FIG. 5, the flexible circuit board 34 would be wound more closely around the peripheral surface 40 by a counterclockwise rotation of the interface portion 16 until it would lie firmly against the peripheral surface 40. On the other hand, the flexible circuit board 34 would be even more loosely arranged by a clockwise rotation of the interface portion 16. Thus, the flexible circuit board 34 can be spooled upon the peripheral surface 40 by a counterclockwise rotation and unspooled by a clockwise rotation of the interface portion. The total range of rotation of the interface portion 16 relative to the housing 14 is limited, in particular, by the length of the flexible circuit board 34 available to be spooled on the peripheral surface 40, and on the capacity of the reservoir 46 to accommodate an unspooled section of the flexible circuit board 34. In the example shown the unspooled section of the flexible circuit board 34 is loosely arranged in the reservoir 46; alternatively, the flexible circuit board 34 may be tensioned by a spring-loaded roll, for example, such that the flexible circuit board 34 lies closely on the peripheral surface 40 independent of rotation angle. Further, in the example shown the flexible circuit board 34 is arranged at an intermediate section of the peripheral surface 40 of the interface portion 16, the intermediate section being spaced from the first end 42 and from the second end 44, and, as is shown in FIG. 4, between the first and second bearings 60a, 60b.

Figure 6:
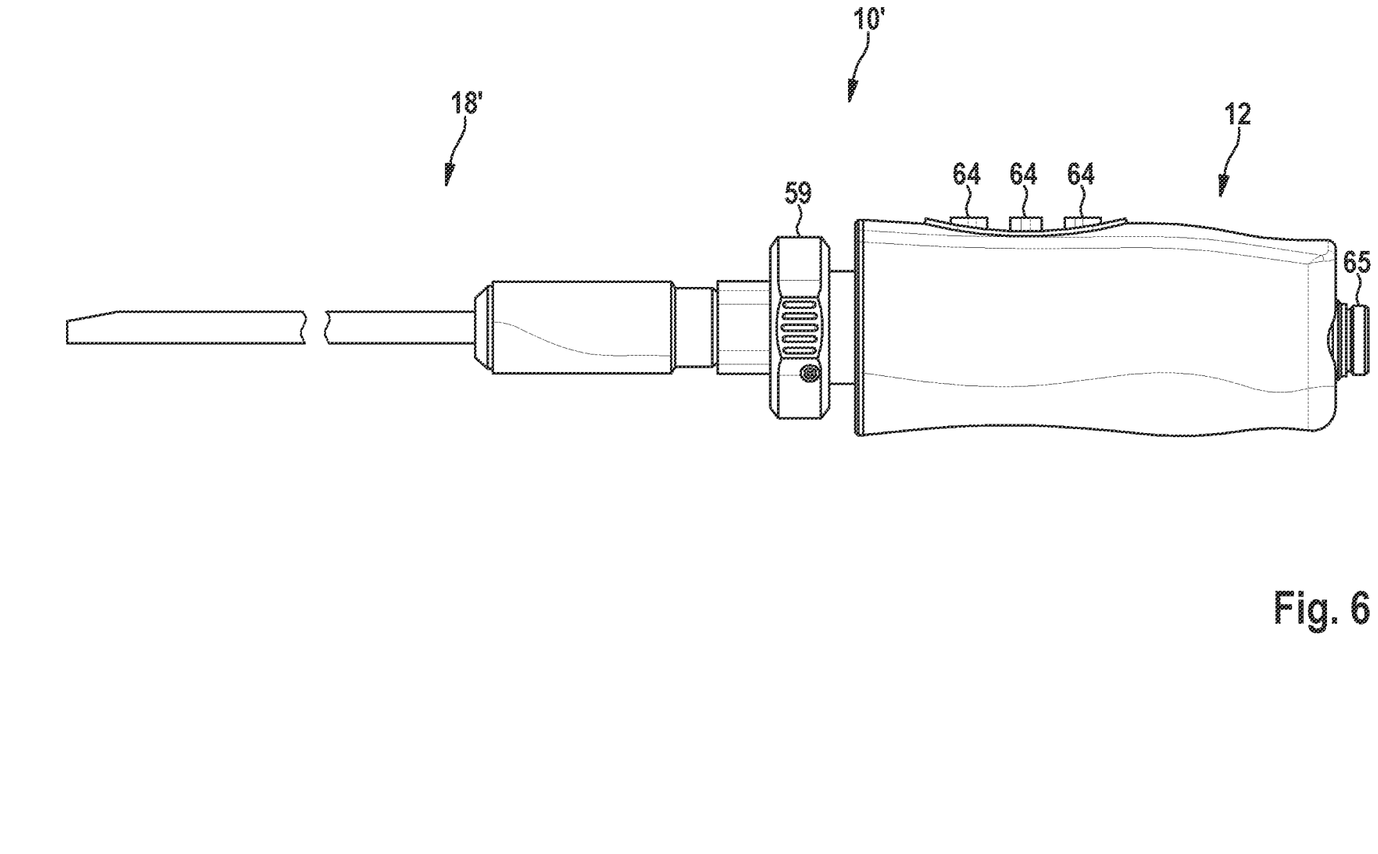
FIG. 6 shows a video endoscope according to a second embodiment of the present invention in a side view.

FIG. 6 shows a video endoscope 10' according to a second embodiment of the present invention, having a shaft 18' that is shown connected to the handle 12. The shaft 18' according to this embodiment is configured like the shaft 18 described above and depicted in FIGS. 1 and 2, but instead of a light post 54 the shaft 18' has a grip wheel 59 that can be gripped by the user to rotate the shaft 18' more easily and accurately. An illumination light source is accommodated in the shaft 18' itself, such as with distally placed LED illumination means. The handle 12 is configured as described above and depicted in a schematic sectional view in FIGS. 1 and 2. As can be seen in more detail in the side view shown in FIG. 6, the handle 12 comprises a multiplicity of control elements 64 with are placed on one side of the handle 12 to be operated by the user generally with the same hand holding the handle 12. Further, a port 65 for passing through or connecting the cable 11 is shown in FIG. 6.

Figure 7:
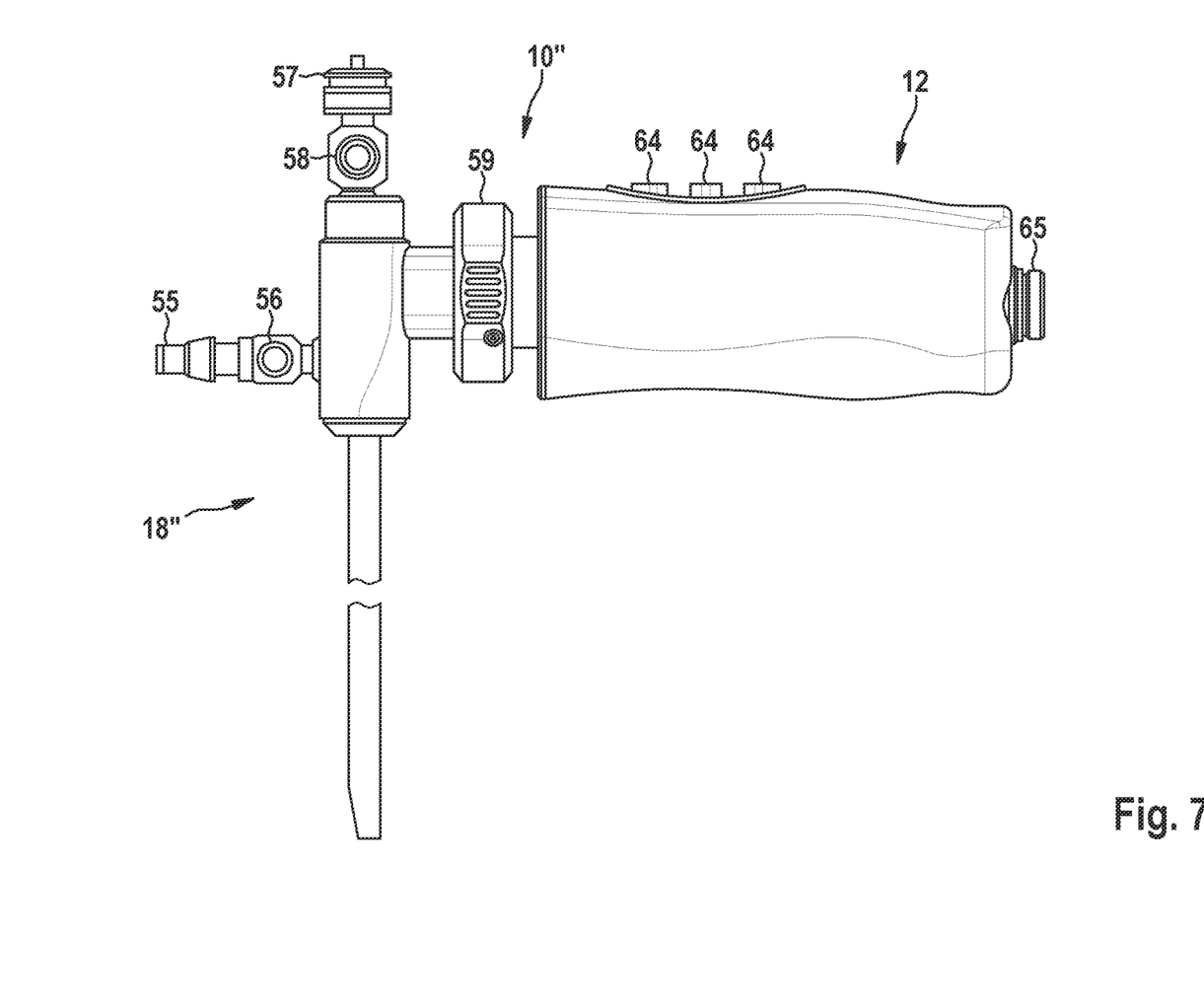
FIG. 7 shows a video endoscope according to a third embodiment of the present invention in a side view.

In FIG. 7 a video endoscope 10" according to a third embodiment of the present invention is shown. The handle 12 is configured as described above and shown in FIGS. 1, 2, and 6. The shaft 18" according to the third embodiment is distinguished from the shaft 18' of the second embodiment in that it is deflected by an angle of 90°, and thus a longitudinal axis of the shaft 18" is at right angles to the rotation axis of the interface unit 16 (see FIGS. 1, 2 and 4). Further, as opposed to the shaft 18, 18' of the first and second embodiments, the shaft 18" of the third embodiment comprises an irrigation channel and an instrument channel Consequently, the shaft 18" has a connector 55 to attach an irrigation hose with an irrigation valve 56, and a port 57 for inserting a working instrument, including a valve 58 for closing the instrument channel when not needed. Like the second embodiment, the shaft 18" has a grip wheel 59 and an integrated illumination light source, instead of a light cable port. As regards other elements, the shaft 18" is configured as described above (see FIGS. 1-3).

The video endoscope 10, 10', 10" according to embodiments of the present invention comprises an electronic image sensor arranged in the shaft 18, 18', 18" and connected via cable 52, second electric connector 28, first electric connector 26, leads 36, PCB 35, leads 37, and flexible circuit board 34 to electric and/or electronic elements provided in the housing 14 (not shown in the figures). Moreover, electric energy and/or control signals can be supplied from the electric and/or electronic elements in the housing 14 to the image sensor or to an illumination source arranged in the shaft, for example. To this end, the electric connections comprise as many leads or conduction tracks as required. Due to the arrangement of the flexible circuit board 34, the electric connection can be maintained in a multiplicity of rotational positions of the shaft 18, 18', 18" relative to the housing 14 of the handle 12. In the housing an image pre-processing unit may be provided to improve data transmission to an external image processing unit via cable 11, for example; however, the video endoscope 10, 10', 10" may be configured such that the housing 14 accommodates only electric leads providing a connection to cable 11. The electric and/or electronic elements mentioned are held stationary in the housing 14 and do not participate in the rotation of the interface portion 16. A sensor signal indicative of a rotation angle or a rotational position of the interface portion 16 with respect to the housing 14 or with respect to a gravity vector may be transmitted to the image pre-processing unit, or to the external image processing unit, and employed to electronically erect the endoscopic image provided by the image sensor. Further, the control elements 64 may be connected to the image pre-processing unit or to an external control unit for controlling various functions of the video endoscope 10, 10', 10", for example relating to illumination, zoom, and/or irrigation. Moreover, the electric and mechanical connection of the shaft 18, 18', 18" to the handle 12 is detachable, improving handling and versatility of the video endoscope 10, 10', 10".

For clarity not all reference numerals are displayed in all figures. If a reference numeral is not explicitly mentioned in the description of a figure, it has the same meaning as in the other figures.

REFERENCE NUMERALS 10, 10', 10" Video endoscope
11 Cable
12 Handle
13 Coupling mechanism
14 Housing
15 Claws
16 Interface portion
17 Front side
18, 18', 18" Shaft
19 Plate
20 Distal end
22 Proximal end
24 Longitudinal axis
26 First connector element
27 Recess
28 Second connector element
29 Connector base
30 Socket
32 Pin
33 Hollow space
34 Flexible circuit board
35 PCB
36 Leads
37 Leads
38 Rotation axis
40 Peripheral surface
42 Front end
44 Rear end
46 Reservoir
48 Rod lens
49 Objective lens system
50 Imaging unit
51 Image sensor
52 Cable
53 Leads
54 Light post
55 Connector
56 Valve
57 Port
58 Valve
59 Wheel
60a Bearing
60b Bearing
61 Seal
64 Control element
65 Port

The invention claimed is:

1. A video endoscope, comprising a handle with a housing and an interface portion rotatably mounted relative to the housing, and an elongate shaft comprising one or more electronic image sensors mounted within the shaft, wherein a proximal end section of the shaft is detachably connected to the interface portion of the handle, and thereby the elongate shaft, and the one or more electronic image sensors mounted therein, are rotatable relative to the handle, wherein the interface portion comprises a first connector element electrically connected to an electric transmission element of the interface portion and the shaft comprises a second connector element electrically connected to the one or more electronic image sensors, the first and second connector elements co-operating to form a detachable electrical connection, and wherein the handle comprises an electrical connection between an exterior of the interface portion and at least one stationary electric and/or electronic component of the handle in a multiplicity of rotational positions of the interface portion relative to the housing.

2. The video endoscope of claim 1 wherein the electrical connection between the exterior of the interface portion and the at least one stationary electric and/or electronic component of the handle comprises at least one sliding contact.

3. The video endoscope of claim 1 wherein the electrical connection between the exterior of the interface portion and the at least one stationary electric and/or electronic component of the handle is arranged at a periphery of the interface portion.

4. The video endoscope of claim 3 wherein the electrical connection between the exterior of the interface portion and the at least one stationary electric and/or electronic component of the handle comprises at least one flexible conductor element configured to be spooled on and/or unspooled from the periphery of the interface portion by rotating the interface portion relative to the housing.

5. The video endoscope of claim 4 wherein the flexible conductor element is or comprises a flexible cable, a flexible ribbon cable and/or a flexible circuit board.

6. The video endoscope of claim 4 wherein the housing comprises a reservoir for receiving at least an unspooled portion of the flexible conductor element.

7. The video endoscope of claim 5 wherein the housing comprises a reservoir for receiving at least an unspooled portion of the flexible conductor element.

8. The video endoscope of claim 7 wherein the unspooled portion of the flexible conductor element is guided by at least one roll, wherein the roll preferably is movably arranged within the reservoir and most preferably is spring loaded in a direction for tensioning the flexible conductor element.

9. The video endoscope according to claim 8 wherein at least a section of the unspooled portion of the flexible conductor element is laid in an arc-like shape in the reservoir and/or is loosely arranged within the reservoir.

10. The video endoscope of claim 9 wherein the handle comprises at least two bearings for rotatably supporting the interface portion wherein the electrical connection between the exterior of the interface portion and the at least one stationary electric and/or electronic component of the handle is arranged at an intermediate section of the periphery of the interface portion, the intermediate section being located between the at least two bearings.

11. The video endoscope of claim 10 wherein a range of rotation of the interface portion relative to the housing is limited by a stop.

12. The video endoscope of claim 4 wherein the handle comprises at least one sensor for detecting a rotation angle and/or a rotational position of the interface portion relative to the housing.

13. The video endoscope of claim 12 wherein the second connector element comprises a plurality of conductor pins and the first connector element comprises a plurality of sockets configured to receive the conductor pins.

14. The video endoscope of claim 4 wherein the shaft is hermetically sealed and/or autoclavable.

15. The video endoscope of claim 4 wherein the shaft comprises an electric illumination source supplied with electric energy via the interface portion.

16. The video endoscope of claim 15 wherein the one or more electronic image sensors is or are arranged in a distal end section of the shaft, or the one or more image sensors is or are arranged in the proximal end section of the shaft and an optical image transmission system extends through the shaft to transfer image light to the one or more image sensors.

17. A handle for a video endoscope, comprising a housing and an interface portion rotatably mounted relative to the housing, wherein the interface portion comprises a first connector element connected to an electric transmission element of the interface portion and connectable to a second connector element of a shaft of the video endoscope, to form a detachable electrical connection, the detachable electrical connection configured to receive an image data from the video endoscope and provide an electrical power to the video endoscope, and wherein the handle comprises an electrical connection between an exterior of the interface portion and at least one stationary electric and/or electronic component of the handle in a multiplicity of rotational positions of the interface portion relative to the housing.

18. The handle of claim 17 wherein the electrical connection between the exterior of the interface portion and the at least one stationary electric and/or electronic component of the handle comprises at least one flexible conductor element configured to be spooled on and/or unspooled from a periphery of the interface portion by rotating the interface portion relative to the housing.

19. The handle of claim 18 wherein the flexible conductor element is or comprises a flexible cable, a flexible ribbon cable and/or a flexible circuit board.

20. The handle of claim 19 wherein the housing comprises a reservoir for receiving at least an unspooled portion of the flexible conductor element.

* * * * *